United States Patent [19]
Aebischer et al.

[11] Patent Number: 6,140,089
[45] Date of Patent: Oct. 31, 2000

[54] CHITOSAN CORE MATRIX CONTAINING CELLS ENCAPSULATED IN A THERMOPLASTIC SEMIPERMEABLE MEMBRANE

[75] Inventors: Patrick Aebischer, Chemin de Plantaz, Switzerland; Beth A. Zielinski, East Greenwich, R.I.

[73] Assignee: Brown University Research Foundation, Providence, R.I.

[21] Appl. No.: 09/251,004

[22] Filed: Feb. 16, 1999

Related U.S. Application Data

[60] Division of application No. 08/294,149, Aug. 22, 1994, Pat. No. 5,871,985, which is a continuation-in-part of application No. 08/176,323, Jan. 3, 1994, abandoned, which is a continuation of application No. 07/952,249, Sep. 28, 1992, abandoned.

[51] Int. Cl.⁷ .......................... C12N 11/10; C12N 11/04; C12N 5/00
[52] U.S. Cl. ....................... 435/178; 424/93.7; 435/182; 435/382
[58] Field of Search ................... 435/177, 178, 435/182, 395, 382; 424/93.7

[56] References Cited

U.S. PATENT DOCUMENTS

| | | | |
|---|---|---|---|
| 4,167,447 | 9/1979 | Masri et al. | 435/178 |
| 4,803,168 | 2/1989 | Jarvis, Jr. | 435/395 |
| 4,892,538 | 1/1990 | Aebischer et al. | 424/424 X |
| 5,158,881 | 10/1992 | Aebischer et al. | 435/180 X |
| 5,871,985 | 2/1999 | Aebischer et al. | 435/178 |

FOREIGN PATENT DOCUMENTS 8702703 5/1987 WIPO.

*Primary Examiner*—David M. Naff
*Attorney, Agent, or Firm*—Mintz, Levin, Cohn, Ferris, Glovsky and Popeo; Ivor R. Elrifi; John Prince

[57] ABSTRACT

Encapsulated viable cells for implanting are prepared having cells dispersed in a particulate, essentially non cross-linked chitosan core matrix that is enclosed within a semipermeable membrane. The cells are entrapped between chitosan particles of the core matrix and there is essentially no interfacial cross-linking between the core matrix and the membrane. The core matrix provides a physical support for the cells such that the cells are evenly dispersed throughout the core matrix so as to allow their maintenance, growth, proliferation and differentiation. The encapsulated cells may be prepared by mixing viable cells with a solution of chitosan, encapsulating the resultant mixture in a thermoplastic semipermeable membrane, and causing the chitosan to precipitate such as by changing the pH to form the core matrix. Alternatively, the chitosan in solution is precipitated to form the core matrix containing cells, and the core matrix is encapsulated in a semipermeable membrane. Cells encapsulated include neurosecretory cell lines, β-cell-derived cells lines, fibroblasts, myocytes and glial cells.

4 Claims, 2 Drawing Sheets

CHITOSAN CORE MATRIX CONTAINING CELLS ENCAPSULATED IN A THERMOPLASTIC SEMIPERMEABLE MEMBRANE

This application is a division of application Ser. No. 08/294,149, filed Aug. 22, 1994, now U.S. Pat. No. 5,871,985, which is a continuation-in-part of application Ser. No. 08/176,323, filed Jan. 3, 1994, now abandoned, which is a continuation of application Ser. No. 07/952,249, filed Sep. 28, 1992, now abandoned.

BACKGROUND OF THE INVENTION

The technical field of this invention is a particulate chitosan core matrix for viable cells encapsulated in vehicles intended for implantation into an individual.

A number of substances have been employed as core material for the encapsulation of cells in microspheres and macrocapsules. Typically, the core material is formed in a gel in which the cells are imbedded. The gelled core may then be further encapsulated in a semipermeable membrane to form an implantable vehicle.

The ideal core material would provide a physical support for the cells to keep them evenly dispersed throughout the core. If cells tend to clump within the core, the cells in the middle of the clump may be deprived of oxygen and other nutrients and become necrotic. The core matrix should also be sufficiently permeable to substances secreted by the cells so that a therapeutic substance can diffuse out of the core and into the tissue or blood stream of the recipient of the implanted vehicle. If proliferation or differentiation of cells within the core is desired, the core matrix should also provide a physio-chemical environment which promotes those cellular functions.

One commonly employed core material is the anionic polysaccharide gum, sodium alginate, as disclosed in U.S. Pat. Nos. 4,352,883 (Lim, F.), U.S. Pat. No. 4,689,293 (Goosen, M. F. A., et al.), U.S. Pat. No. 4,806,355 (Goosen, M. F. A., et al.), U.S. Pat. No. 4,789,550 (Hommel, M., et al.), U.S. Pat. No. 4,409,331 (Lim, F.), and U.S. Pat. No. 4,902,295 (Walthall, B. J., et al.).

Other core materials include collagen (U.S. Pat No 4,495,288, Jarvis, A. P. et al.), agar, agarose, fibrinogen (U.S. Pat. No. 4,647,536, Mosbach, K., et al.), and fibronectin or laminin (U.S. Pat. No. 4,902,295, Walthall, B. J., et al.).

The core material of the present invention is chitosan, which is a derivative of chitin. Chitin is the major component of the shells of shrimp and crab, and is produced commercially as a by-product of the shellfish industry.

Chitin is a linear polymer comprised of 2-acetylamino-D-glucose units. The term "chitosan" refers to a family of polymers, derived from chitin, that have been partially deacetylated to provide sufficient free amino groups to render the polymer soluble in selected aqueous acid systems (Filar., L. J., et al., Hercules Research Center Contribution No. 1697, Wilmington, Del.). Chitosan is commercially available in varying degrees of deacetylation ranging upwards from less than 75%. The degree of solubility of chitosan with a given degree of deacetylation depends on polymer molecular weight, temperature, and concentration and nature of the acid solvent (Filar, L. J., et al. supra).

Chitosan was reportedly used experimentally as a dura mater substitute (Muzzarelli, R., et al., 1988 Biomaterials 9:247–252). The dura mater is the sheet of collagenous connective tissue which encases the brain within the skull. The success of chitosan in this experimental paradigm was attributed to the fact that its structural characteristics are similar to the glycosaminoglycan components of naturally occurring extra-cellular matrix. In the presence of chitosan, fibroblasts and mesenchymal vascular cells in the surrounding tissue were stimulated to migrate, proliferate, and differentiate. These cellular activities are essential components of wound healing and tissue-rebuilding. Chitosan has also been reported to be effective in bone-repair and as a suture material (Sapelli. P. L., et al. 1986 in *Chitin in Nature and Technology* Eds. R. A. A. Muzzarelli, et al., Plenum Press, N.Y.: Nakajuma, M., et al. 1986 *Jpn J Surg* 16:418–424).

A feeding solution containing liquid chitosan was added to growing myocyte cultures and reportedly enabled the three-dimensional growth of the myocytes in culture plates (Malette, W. G., et al. U.S. Pat. No. 4,605,623). A chitosan/collagen material was reportedly effective in promoting cell substrate adhesion and proliferation in culture (Miyata, T., et al. EP 0318286).

Chitosan has been used to form a depot for the sustained release of pharmacologically active macromolecules such as hormones, enzymes, and protein antigens (Cardinal, J. R., et al. U.S. Pat. No. 4,895,724).

Processes have been disclosed for using chitosan to encapsulate living cells (Daly, M M., et al. U.S. Pat. No. 4,808,707; Rha, C.-K., et al., U.S. Pat. No. 4,744,933; Rha, C.-K., et al., U.S. Pat. No. 4,749,620; Schroder, U., U.S. Pat. No. 4,713,249; Jarvis, A. P., U.S. Pat. No. 4,803,168). These processes are based on the cross-linking of the cationic free amino groups of chitosan via ionic bonds with anionic species such as phosphate ions or anionic polymers such as alginate. The terms "cross-linking", "cross-linked", etc. as defined herein mean ionic bonds or bridges between distinct chitosan chains or between distinct regions of a single chain.

The capsules of Rha are formed by dropping cationic chitosan solution into anionic alginate solution. The positively charged free amino groups of the chitosan polymers on the surface of the chitosan droplet are attracted to the negatively charged carboxylate groups of the alginate polymers, forming cross-links at the interface between the chitosan droplet and the alginate solution. The interfacially cross-linked chitosan-alginate forms a membrane enclosing a liquid chitosan core. Daly uses similarly interfacially cross-linked chitosan in which the composition of the alginate used is varied in order to alter the permeability properties of the capsule membrane. The microcapsules of Jarvis are formed by cross-linking the core chitosan polymers by the addition of divalent or multivalent anions, then forming permanent interfacial cross-links at the outer surface to a polymer having plural anionic groups, such as polyaspartic or polyglutamic acid. The inner core of the Jarvis capsules may be used in the cross-linked state, or may be reliquefied by the addition of low molecular weight cations. In all of these cases, the principal function of chitosan is to serve as one half of a pair of charged polymers which form interfacial cross-links resulting in the formation of the capsule membrane or wall.

The chitosan matrices of Schroder, supra, are formed through crystallization of the carbohydrate polymer to form a polymeric lattice. The capsules thus formed are used to deliver non-living biologically active substances. The methods employed for crystallization are generally considered too harsh for the encapsulation of living cells.

A major commercial producer of chitosan, Protan Laboratories, has published several protocols for the immobilization of cells within chitosan gels. These methods all employ ionotropic gelation (i.e. cross-linking) of chitosan by combining the chitosan/cell solution with anionic species. Proposed anions include polyphosphates, alginate, carrageenan, and fatty acids with sulfate moieties. (Technical bulletin: *Chitosans for Cell Immobilization*, Protan Laboratories, Redmond, Wash.). Cross-linked chitosan, however, has not been used as a core matrix for viable cell encapsulation in capsules with thermoplastic jackets. Nor has non cross-linked particulate chitosan ever been used as a core matrix for living cell encapsulation in encapsulation devices.

An object of this invention, therefore, is to provide a novel non cross-linked particulate chitosan core matrix for living cell encapsulation in encapsulation devices.

Another object of this invention is to provide a particulate chitosan core matrix in capsules with thermoplastic jackets where formation of the capsule wall is not dependent upon the presence of the chitosan matrix (e.g. through interfacial cross-linking) so that the properties of either the jacket or the matrix may be varied without concern for effects on each other.

Additional objects and features of the invention will be apparent to those skilled in the art from the following detailed description and appended claims when taken in conjunction with the figures.

SUMMARY OF THE INVENTION

An encapsulation device is described having a particulate, essentially non cross-linked chitosan core matrix enclosed in a permeable or semipermeable jacket. The device is useful for maintaining, growing, proliferating, and differentiating viable cells which are entrapped between the chitosan particles of the core matrix.

A method for making the encapsulation device is disclosed wherein a solution of chitosan is prepared and then mixed with viable cells. The chitosan/cell mixture is then encapsulated with a permeable or semipermeable jacket to form a tissue implantable encapsulation device. The chitosan is then precipitated to form a particulate chitosan core matrix with the viable cells dispersed therein. Alternatively, the chitosan is precipitated by the addition of the viable cells prior to encapsulation.

The viable cells that find particular use in this invention comprise cells selected from the group consisting of neurosecretory cell lines, β-cell-derived cell lines, fibroblasts, myocytes, and glial cells.

DETAILED DESCRIPTION OF THE INVENTION

Figure 1:
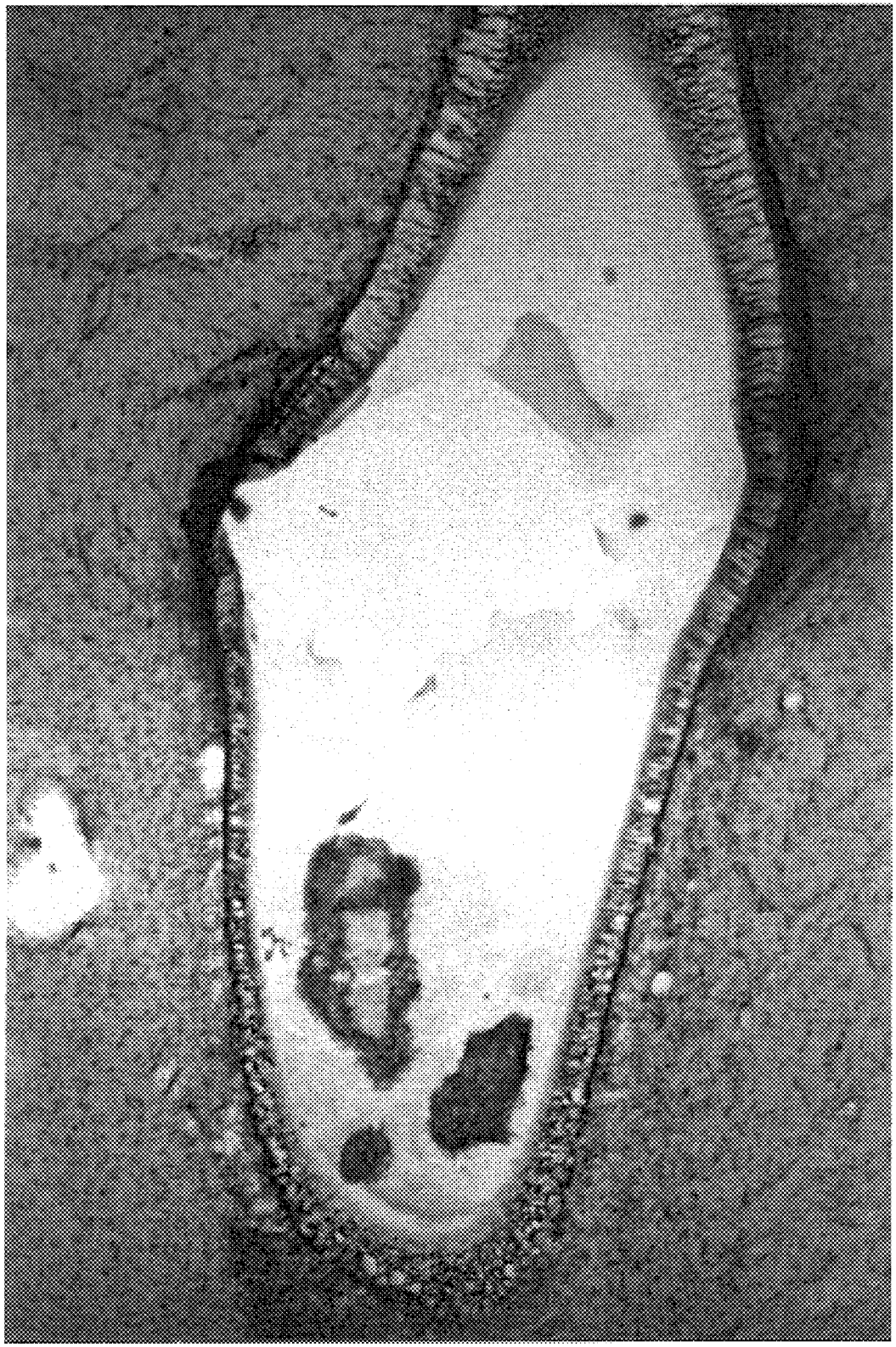
FIG. 1 represents a histological section of a thermoplastic macrocapsule containing PC12 cells implanted into the brain of a cynomologous monkey. The capsule contains no core matrix.

The present invention is based on the discovery that, chitosan may be formed into a three-dimensional, particulate matrix for incorporation into cell encapsulation devices. The chitosan core matrix of the present invention results from the use of a discrete chitosan particle without substantial cross-linking or other chemical attachments between particles.

While the precipitate of the present invention is formed substantially in the absence of cross-linking agents, and is essentially uncross-linked, it should be born in mind that there are likely to be free charges on the precipitate surface which remain available for cross-linking under the appropriate conditions. The terms "without substantial cross-linking" or "essentially non cross-linked", etc. for purposes of this invention refer to the total assemblage of the chitosan within an encapsulation device, such that the chitosan is particulate in nature and the individual polymer chains are not covalently connected or ionically cross-linked into a single or a few gel-like structures.

The chitosan core matrices of the present invention entrap cells between particles but not within a continuous three-dimensional matrix as within a cross-linked gel structure (e.g. alginate in the presence of ionic calcium). Such particulate chitosan matrices may be produced by pH dependent precipitation of soluble chitosan substantially in the absence of cross-linking agents. The particulate chitosan matrices may also be produced by placing chitosan-containing capsules in any substantially non-toxic solution having a sufficient ionic content to mask enough of the charges on the chitosan to cause precipitation. Suitable solutions are biological buffers that optionally contain monovalent anions to speed up the rate of precipitation.

The term "cross-linked chitosans" for the purposes of this invention refers to solids or gels that depend upon ionic interactions between polymer chains to retain their solid or gel-like character. Cells in such gels are embedded within a more or less continuous three-dimensional matrix formed by the interconnection of chitosan chains. Cross-linked chitosans are generally formed in the presence of cross-linking agents.

Interfacial cross-links are not the subject of the current invention, and while their formation is not prescribed, their existence generally will not affect the operation of the invention. In other embodiments, minute particles of cross-linked chitosan with essentially no cross-links occurring between particles may be used to form the particulate chitosan matrix. Such particles are formed by the dehydration of cross-linked chitosan gels, and subsequent pulverization (e.g. with mortar and pestle) of the resultant structure to particles less than 100 μm in diameter, preferably less than 50 μm and most preferably less than the size of the cells to be entrapped by them.

In embodiments involving production of particulate chitosan by precipitation, the chitosan precipitation is preferably achieved by placing the chitosan-containing capsules in a buffered solution containing one or more substantially non-toxic monovalent ions such as phosphate, chloride, bicarbonate, iodide or bisulfate. The amount of ions needed for precipitation to occur can be very easily determined by one of ordinary skill in the art, for example, by a titration experiment. Precipitation can also occur by adjusting the pH of the chitosan solution. Virtually any method which removes or masks the charge of a sufficient number of the free amino groups of the chitosan should be suitable. Such methods can involve the reaction of the amino groups with organic substances. Alternately, biocompatible non-chitosan reactive water soluble polymers may be used to induce precipitation. The precipitate provides cell separation and a charged surface for cell interaction. The core matrix is then encapsulated within a membrane or jacket that, upon culture or implantation in an individual, will allow diffusion of nutrients, waste materials, and secreted products, but which is preferably immunoisolatory and blocks the cellular and molecular effectors of immunological rejection. Preferably there is no type of chemical or physical interlinking or bonding between the core matrix and the jacket.

As defined herein, the term "individual" refers to a human or animal subject. The term "tissue" as defined herein refers to cells, cell aggregates, tissue or tissue fragments from either animals or humans.

Chitosan is available from a number of manufacturers and may vary in its purity and % deacetylation both between lots and between manufacturers. Despite the slight differences in solubility properties, many of these chitosans will be useful in the instant invention. However it should be born in mind that the pH-dependent solubility characteristics should be confirmed for any given lot of chitosan. For example, the solubility characteristics of Fluka chitosan flakes in 6 mM HEPES and Protan Seacure Cl have been compared. The Fluka chitosan precipitates at pH>6.3 whereas the Protan chitosan precipitates near pH 6.8.

In one embodiment, the chitosan matrix-forming material is prepared as a soluble solution, mixed with cell-containing media, and then used in a co-extrusion process to form thermoplastic or form-holding encapsulation devices such as fibers or flat sheets. In other embodiments, the chitosan/cell solution is introduced into preformed devices. The matrices of the invention may also be used in the formation of microspheres and for post-production filling of preformed fibers and/or capsules.

The chitosan matrix of the present invention is compatible with several cell types useful in implantable vehicles for the treatment of diseases such as diabetes, Parkinson's disease, and other neurological disorders. In addition, encapsulated myoblasts may be useful as sources of trophic or sprouting factors for supporting peripheral nerve repair or regeneration.

Herein, the term "core matrix" refers to a biocompatible, three-dimensional structure which supports and may enhance cell proliferation and/or cell differentiation.

The chitosan core matrix of the invention is comprised of particulate chitosan which provides or acts as an irregular scaffolding into which cells are free to grow. The matrix provides a large growth area which does not restrict the cells' ability to divide and expand.

Cells which grow well in the matrix of the present invention include CHO cells, fibroblasts, myocytes, neurosecretory cells such as PC12 cells, pancreatic β-cells such as NIT and RIN cell lines, and glial cells such as astrocytes. Cells compatible with the chitosan matrix may be genetically engineered to secrete a desired substance which is heterologous to the compatible cell. For instance, fibroblasts which have been genetically engineered to secrete nerve-growth factor (NGF) are compatible with the present chitosan matrix.

Chitosan is characterized as a poly-n-glucosamine, with a large number of free amino groups. Chitosan is commercially available in a number of forms differing in their number of free amino groups (% deacetylation), degree of purity, molecular weight distribution, and viscosity. In practicing the invention, a preferred type of chitosan has a molecular weight range of 10–1,000 kd preferably 100–300 kd. Lower molecular weight distributions may also be useful.

Preferably, the chitosan has a degree of deacetylation of about 80% to about 90%, preferably 80–85%. A higher degree of deacetylation correlates with a higher number of free amino groups, which are positively charged. Percent deacetylation is important in the regulation of the pH sensitive precipitation of chitosan from the cell/growth media of the current invention. Specifically, chitosans having <50% deacetylation demonstrate solubility over a broader range of pHs (e.g., pH 2 to 11), whereas 80% deacetylated chitosan (Seacure Cl Protan) is soluble at pH 6.3 and precipitates at pH 6.8.

Viscosities for soluble 1% chitosan at pH 4.0 of about 20–80 cp is preferred. The molecular weight distribution of the various uncross-linked chitosan polymer chains within a specific chitosan preparation or lot significantly affects the viscosity of a solution of a given concentration. Additionally, solids (e.g., salts, carbohydrates) or copolymers present in the chitosan solution as well as the actual concentration of the chitosan solution itself, will have significant effects on the viscosity.

Viscosity of the chitosan solution effects the ability to load encapsulation devices, and the speed of precipitation. This has a number of practical consequences for device fabrication and loading. Mechanized capsule fabrication such as the coextrusion process described in U.S. Pat. No. 5,158,881, Aebischer, et al., requires lower viscosity chitosan solutions in the range of 10–150 cps (~0.5–2% chitosan), as compared to device fabrication involving manual introduction of the cell/chitosan solution through syringes, etc. where viscosity is a far less critical limitation and can be as great as 1,000 cps (~5–10% chitosan).

In one embodiment, to form the core matrix of the invention, the chitosan is first dissolved in an aqueous acid solution, approximate pH 2–pH 4. A variety of acids such as malic acid, citric acid, succinic acid, ascorbic acid, acetic acid or hydrochloric acid may be used to make the aqueous acidic solution. Chitosan is available from several sources (Fluka Chemical Corp., etc.). A preferred source of chitosan is Protan's SeaCure Cl.

Following dissolution of the chitosan in the acidified solution, the pH is raised to a level that is close enough to physiological pH to be tolerated by cells, but still low enough to maintain the solubility of the chitosan. Preferably, the chitosan solution is brought to about pH 6.3–6.5 using a biocompatible buffer such as HEPES, TRIS, or monobasic phosphate. Table 1 summarizes the properties of a number of biologically compatible buffers which may be used in this system. It is advisable to select a relatively weak buffering agent with a useful buffering range that encompasses the pH of precipitation of the chitosan solution. The use of a weak buffer facilitates the adjustment of pH to 7.4 necessary for initiation of chitosan precipitation, as well as the preservation of cell viability (the exposure of cells to pHs other than 7.4 should be minimized). For purposes of this invention, chitosan precipitation occurs preferably in the range of pH 6.5–6.8, the exact value will vary depending upon the degree of acetylation and counter ions present for the particular lot of chitosan used. Therefore, it is always useful to characterize the precise pH conditions for precipitation with a new lot of chitosan. If phosphate buffers are used they should be monobasic. Multi-phosphates should be avoided because groups such as tripolyphosphate lead to undesirable levels of chitosan cross-linking.

TABLE I

Suitable Buffers

| Buffer | Buffering range |
|---|---|
| BES | 6.2–7.6 |
| BIS-TRIS | 5.7–7.1 |
| HEPES | 6.6–8.0 |
| PIPES | 6.0–7.4 |
| TAPSO | 6.8–8.0 |
| TES | 6.5–7.9 |

The chitosan solution is then mixed (approximately 1:1 vol/vol) with cells suspended in their growth media. In order to minimize undesirable cross-linking, all growth media used in this invention should have minimal or no negatively charged polyelectrolytes (e.g., alginate) or multivalent anions (e.g., polyphosphate) present. The presence of cells within the growth medium will contribute additional buffering effects so empirical testing should be performed to establish the optimal buffering required for precipitation of the chitosan.

The cells mixed with solubilized chitosan are then enclosed in implantation vehicles which are either microspheres or macrocapsules. Microspheres may be formed according to any methods of Sefton, U.S. Pat. No. 4,353,888. When macrocapsules are to be formed, the preferable methods are disclosed in U.S. Pat. No. 5,158,881, to Aebischer et al.

The implantation vehicle is then placed in growth media having a pH of about 7.4, which causes the chitosan to precipitate. The precipitated chitosan thus forms a particulate three-dimensional matrix inside the microsphere or macrocapsule, with the cells embedded therein.

In another embodiment, solid chitosan is present in the cell solution prior to loading cells into the capsule. In this embodiment the particulate size of the solid chitosan must be compatible with loading into the capsule. Addition of soluble chitosan to the cell solution and adjusting the pH so that the chitosan precipitates from the solution, generally leads to a flocculent precipitate. The cells and the precipitated chitosan may then be mixed or stirred to a suspension and loaded directly into capsules.

The use of chitosan in thermoplastic or other devices where formation of the capsule wall and/or permselective properties of the device is not dependent upon the presence of the chitosan matrix (e.g. through interfacial cross-linking), means the properties of either the outer membrane (i.e., jacket) or the matrix may be varied without concern for effects on the other. Thus, the molecular weight cutoff of the outer jacket may be modified without compensatory or similar changes in the chitosan core material. Likewise the identity and properties of the chitosan (e.g., percent deacetylation, viscosity, molecular weight distribution) used for formation of the matrix may be selected on the basis of its effects on cell functionality and viability alone. It is not necessary to similarly verify its effects on the properties of the device membrane (i.e., as would be necessary in the microsphere devices of Rha U.S. Pat. No. 4,744,933).

Encapsulated PC12 cells may be grown with or without the presence of nerve growth factor (NGF). In either circumstance, the addition of chitosan is beneficial. PC12 cells encapsulated according to the present invention display improved viability with only a small amount of necrosis observed at 8 weeks both in vivo and in vitro. Encapsulated PC12 cells grown in vitro within the chitosan matrices of the present invention and in the presence of NGF differentiate to polygonal cell types and elaborate extensive neurites. This contrasts to PC12 cells encapsulated in the absence of any core matrix which tend to be spheroid in appearance with few, if any, neuritic extensions. Our own studies have also indicated that about 1.5% chitosan cross-linked by triphosphate tends to be too dense to adequately support the growth of cells within a thermoplastic capsule. Many cells, e.g., PC12 cells, normally tend to grow on a single surface in culture and do not prefer spheroidal aggregations as was observed with cross-linked chitosan. Differentiation of PC12 cells may be necessary for the production of some desirable therapeutic substances such as dopamine, as well as to limit cell growth.

Fibroblasts constitute another therapeutically useful cell type which survives and functions best encapsulated in a three-dimensional growth matrix. Fibroblasts are migratory by nature, and they require an appropriate substrate on which to move. Moreover, in order to proliferate fibroblasts require a substrate on which to anchor.

Fibroblasts are a convenient cell host for the expression of certain genetically engineered proteins such as nerve growth factor (NGF). Fibroblasts which secrete NGF may be implanted in a subject for the treatment of chronic progressive neural degenerative conditions such as Alzheimer disease.

NGF-secreting fibroblasts survive well when encapsulated in the chitosan matrix of the present invention. In addition to viability, the chitosan core matrix of the present invention promotes maintenance of function of NGF-secreting fibroblasts. While these fibroblasts in a cross-linked alginate-core capsules lose their ability to secrete NGF after 1 week, the same cells encapsulated in the present chitosan-core vehicle retain their ability to secrete NGF for four weeks.

One of skill in the art of cell culture will be able to identify other useful cell types which may differentiate or proliferate when encapsulated in the chitosan matrix of the present invention.

EXAMPLE 1

Preparation of the Chitosan Solution

High molecular weight chitosan flakes, a 2-amino-2-deoxy-(1→4)-β-D-glucopyranan (Fluka Chemical Corp., Ronkonkoma, N.Y.), were autoclaved under water in order to secure sterility. Following sterilization, 6 g of chitosan was immediately combined with approximately 250 mls of 1% ascorbic acid in 0.8% saline with components vortexed at high speed in an industrial strength Waring 1M blender to yield a final volume of 300 mls. Some chitosan remained insoluble at this point, yielding a final concentration between 1.5 and 2%. Upon completion of two five minute vortexing periods, 50 mls of 60 mM HEPES (N-2-Hydroxyethylpiperazine-N'-2-ethanesulfonic acid, Sigma) buffer solution was prepared in 0.8% saline and added to the chitosan. This step resulted in a final buffering capacity of 10 mM. Refrigeration of the chitosan solution was necessary in order to maintain a pH of 6.3.

EXAMPLE 2

Encapsulation of Fibroblasts

R208F control fibroblasts were cultured in DMEM supplemented with 10% fetal calf serum (Gibco, Grand Island, N.Y.) and 100 units/ml streptomycin/penicillin (Sigma, St. Louis, Mo.). R208N.8 fibroblasts, genetically engineered via infection with a retroviral vector encoded with the sequence for nerve growth factor (NGF) were maintained in DMEM containing 10% fetal calf serum, 1 mg/mil Geneticin (Gibco) and 100 units/ml streptomycin/ penicillin. Geneticin preferentially destroys nontransfected cells in order to maintain a pure culture. Both cell types were maintained at about 37° C. in a water-saturated 5% $CO_2$ incubator. The R208N.8 and R208F cell lines were a gift of X. Breakefield and P. Short.

Prior to encapsulation with chitosan, both the control and the engineered fibroblast cell lines were harvested by incubation with 0.05% trypsin in HBSS for 3 minutes. Following centrifugation at 800 g, $2\times10^6$ cells/ml of cells were resuspended in 200 µl of their respective nutrient media. The cell suspensions were introduced into 300 µl of the chitosan matrix solution prepared according to Example 1 and infused into a polyacrylonitrile/polyvinylchloride fiber (PAN/PVC-fiber) after the method described in Aebischer et al. U.S. Pat. No. 4,892,538. The fiber was segmented into discrete sections and the ends of the fiber were sealed using a heat sealing method. Capsules were then incubated in physiologic saline for a number of washes lasting approximately 5 minutes each, causing the chitosan to precipitate. All cell-containing chitosan capsules were transferred to growth media of which the R208N.8 and the R208F were maintained in a humidified 5% CO2 incubator at 37° C. Similar capsules were prepared using 2% alginate in place of chitosan. The alginate solution was obtained from Kelco HV, Kelco N.J. and was prepared according to Aebischer et al., 1991 *Brain Research* 560:43–49.

The encapsulated cells were maintained in culture for 4 weeks. The cells proliferated within the chitosan during the entire time course, and cell death was minimal.

The encapsulated fibroblasts were bioassayed as follows for biochemical functionality at 2–4 weeks of encapsulation. The bioassay is based on the response of PC12 cells to NGF, which causes neurite extensions to grow out from PC12 cells in the direction of greater concentration of NGF. To test whether the genetically engineered fibroblasts, R208N.8, continued to express and secrete NGF while maintained in the capsules, the capsules were co-cultured for 2 weeks with unencapsulated PC12 cells grown on collagen coated tissue culture plates, and their effect on the PC12 cells was monitored.

After 1 week, neuritic extensions were prominent in both co-cultures of the chitosan-encapsulated R208N.8 and alginate-encapsulated R208N.8. The encapsulated control fibroblasts, R208F, both chitosan and alginate controls, did not have an effect on differentiation of the PC12 cells.

After 2 weeks, the PC12 cells in co-culture with chitosan-encapsulated R208N.8 cells maintained their differentiated state. In contrast, the PC12 cells in co-culture with alginate-encapsulated R208N.8 cells had retracted their neurites and regained their undifferentiated morphology. The encapsulated control fibroblasts remained neurotrophically inactive.

This shows that fibroblasts engineered to express NGF retain their ability to express the heterologous protein when maintained encapsulated in the chitosan matrix of the present invention.

EXAMPLE 3

Encapsulation of PC12 Cells

PC12 cells were cultured in RPMI supplemented with 10% heat inactivated horse serum, 5% fetal calf serum (Hazelton, Lenexa, Kans.) and 100 units penicillin/ streptomycin. Cultures of PC12 cells were grown in a suspension culture in a water-saturated 7% $CO_2$ incubator at 37° C.

PC12 cells were obtained from the culture dish by gentle trituration of the growth medium to generate a cell suspension. Following centrifugation at 800 g, $2\times10^6$ cells/ml of cells were resuspended in 50 µl of their respective nutrient media. The cell suspensions were introduced into 250 µl of the chitosan matrix solution prepared according to Example 1 and infused into a PAN/PVC-fiber as in Example 2. The fiber was segmented into discrete sections and the ends of the fiber were sealed using a heat sealing method. Capsules were then incubated in physiologic saline for 3 minutes, causing the chitosan to precipitate. Cell-containing chitosan capsules were transferred to growth media and maintained in a humidified 7% $CO_2$ incubator at 37°. Similar capsules were prepared using 2% alginate in place of chitosan.

Encapsulated PC12 cells were maintained in culture for 4 weeks, during which time the cells proliferated within the chitosan matrix, and cell death was minimal. PC12 cells, under potassium stimulated conditions, released in the range of 1–2 nanomolar concentrations of dopamine at 4 weeks. PC12 in capsules with alginate cores were also viable after 4 weeks. However, cells occurred in small spheroid clusters within the alginate. There were little or no neuritic extrons visible.

EXAMPLE 4

In Vivo Viability of PC12 Cells Encapsulated in the Presence of a Precipitated Chitosan Matrix PC12 cells have previously been encapsulated in the absence of a core matrix and implanted in the brains of rodents and non-human primates. Cells survive and can ameliorate Parkinsonian symptoms in a number of model systems. However, in the absence of core matrices the PC12 cells clump, forming large clusters which develop necrotic cores and do not extend significant neuritic processes. The present experiments were designed to compare the performance and growth characteristics of PC12 cells grown in the presence or absence of precipitated chitosan core matrices.

PC12 cells were grown in suspension cultures, harvested, rinsed with RPMI medium, centrifuged and the supernatant decanted.

4.4 g of Fluka High MW chitosan was dissolved in 150 mls of sterile 0.85% saline at 70° C., using vigorous stirring. The pH of the solution was adjusted to 6.2 using 45 ml of 100 mM HEPES buffered saline (pH 8.0). The solution was sterile filtered through a 0.22 µm millipore filter.

The chitosan solution was mixed with an equal volume of RPMI and used to resuspend the cell pellet to a concentration of $5\times10^6$ cells/ml. The cells/chitosan solution (~1,000 µl) was coextruded with PAN/PVC into PAN/PVC semipermeable fiber (~700 µm ID, ~950 µm OD, MWCO ~60 Kd). Fibers were trimmed to appropriate dimensions (1.1±0.1 cm) and sealed by crimping the ends and applying heat for closure. Seals were then capped in PAN/PVC (15 g PAN/ PVC:85 g DMSO). Cells were held in culture in RPMI plus 6 µm insulin for 24–48 hours prior to implantation.

Control capsules were prepared using the same procedure except that Hepes buffered saline without chitosan was used.

Encapsulated PC12 cells were implanted into the basal ganglia of ketamine anesthetized cynomologous monkeys. A craniotomy was performed using constant irrigation with 0.9% sterile saline. Injection coordinates were (relative to midline)

C1=21.0 mmA×4.5 mmL (14.5 mmV)

P1=23.0 mmA×9.0 mmL (14.0 mmV)

P2=19.0 mmA×10.0 mmL (12.0 mmV)

P3=15.5 mmA×11.5 mmL (13.0 mmV)

The tip of a teflon cannula, specifically designed to accommodate a capsule with minimal clearance, containing an obturator was positioned to the appropriate coordinates in the striatum. The obturator was removed and the capsule was placed into the cannula and deposited into the striatum. The cannula was then removed, three additional capsules were similarly placed in adjacent striatal regions. Following implantation the dura was closed and skull flap replaced and secured and sutured.

Four weeks following implantation capsules were retrieved and histological analysis performed. In those capsules containing the chitosan core matrix of the present invention, cells were viable and small clusters were distributed along the length of the capsule. In capsules without chitosan cores, PC12 cells were aggregated in large clusters with necrotic cores.

Figure 2:
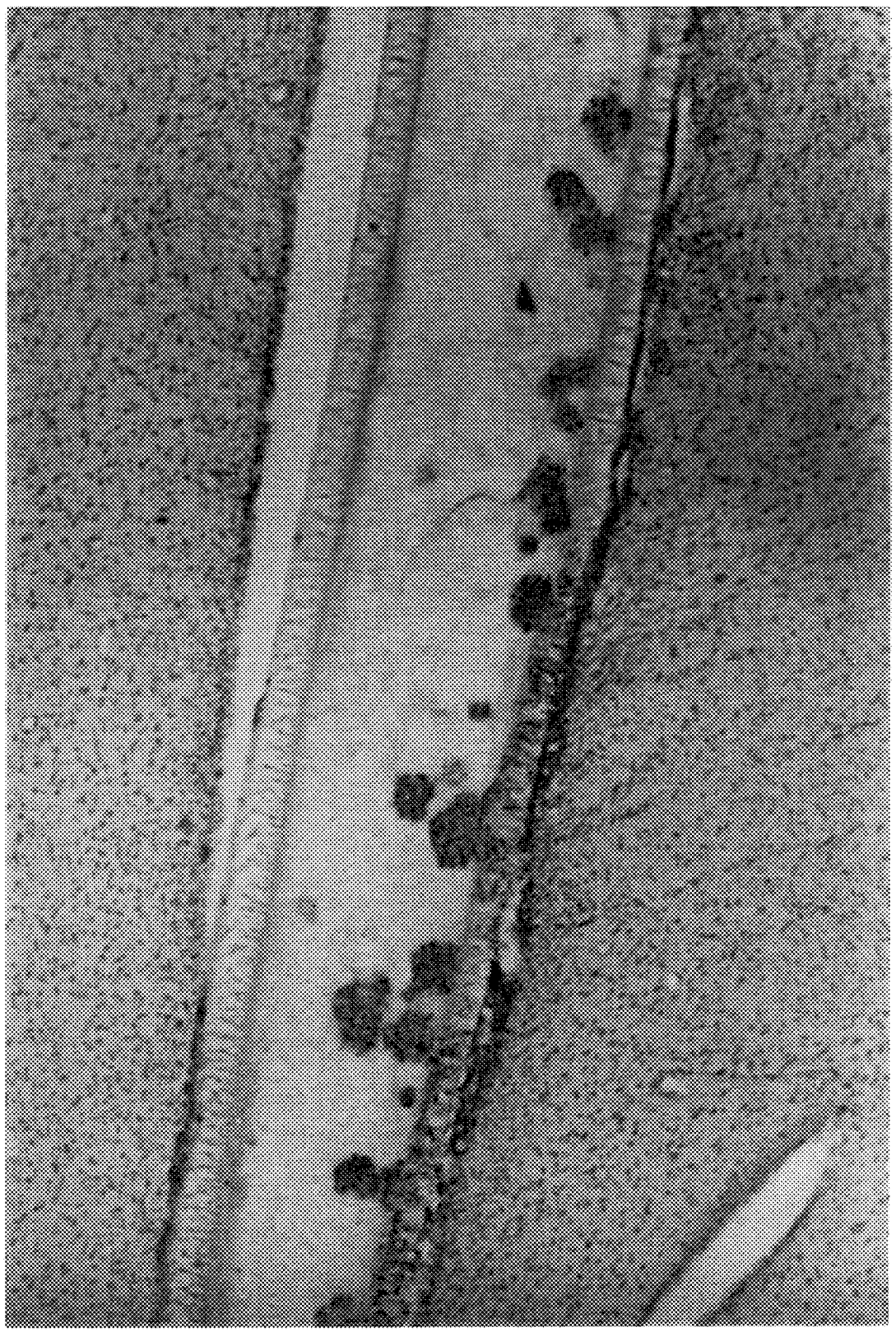
FIG. 2 represents a histological section of an implanted thermoplastic macrocapsule containing PC12 cells embedded in the particulate chitosan core matrix of the present invention.

The improved viability of PC12 cells in the chitosan matrix of the present invention is easily seen in a comparison of FIG. 1 and FIG. 2. FIG. 1 shows very large clusters of PC12 cells from a thermoplastic capsule implant without a core matrix. Several white necrotic cell cores (i.e., dead cells) are clearly evident in the cell cluster at the upper left. FIG. 2 shows the PC12 cells embedded in the precipitated chitosan core matrix implant of the present invention. In general, the cell clusters in FIG. 2 are much smaller and there is no sign of necrosis.

EXAMPLE 5

Preparation of Precipitated Chitosan Core Matrices for Three Dimensional PC12 Cell Adherence/ Maintenance Pre-Encapsulation 8 mls at $0.5-1 \times 10^6$ cells/ml of PC12 cells were taken from flask cultures (triturated off a rat tail collagen substrate), placed in a 15 ml conical centrifuge tube, and mixed with 2 mls of a 2% chitosan solution (Fluka HV) in 25 mM HEPES in isotonic saline pH 6.4. The cell/chitosan solution was mixed by gentle inversion until a flocculent precipitate was observed.

The cell/chitosan solution was then placed in a 100 mm petri dish and grown in static culture at 37° C., 7% $CO_2$ in PC12 medium. Cells were observed to grow in grape-like clusters within the flocculated precipitated chitosan.

After 5 days in culture, the PC12 cell/chitosan scaffolding was collected by centrifugation at 500×g in conical centrifuge tubes. Under these conditions, single cells remained suspended in the supernatant and the PC12 cells/chitosan complex pelleted. Half the medium was then decanted and replaced with fresh medium (without chitosan). The PC12 cell/chitosan complex was either replated at this point or suspended and loaded into preformed PAN/PVC capsules at a density of $5-10 \times 10^6$ cells/ml.

EXAMPLE 6

Precipitation of Chitosan in a Biological Buffer Containing Monovalent Anions

A solution of chitosan was prepared using the procedure outlined in Example 1. Fibroblasts were encapsulated with the chitosan using the procedure outlined in Example 2. The cell/chitosan solution was loaded into pre-formed fibers. The loaded fibers were placed in Hanks' Balanced Salt Solution (HBSS) with extra $KH_2PO_4$ added (from 60 mg/L to 100 mg/L) to speed up precipitation of the chitosan. The buffer contained the following: 186 mg/L $CaCl_2 \cdot 2H_2O$, 400 mg/L KCl, 100 mg/L $KH_2PO_4$, 200 mg/L $MgSO_4 \cdot H_2O$, 8 g/L NaCl, 350 mg/L $NaHCO_3$, 90 mg/L $Na_2HPO_4 \cdot 2H_2O$, and 1 g/L glucose. The capsules were left in the HBSS for five minutes, during which time precipitation occurred. Precipitation also occurs in HBSS alone (without additional $KH_2PO_4$), but at a slower rate.

What is claimed is:

1. Encapsulated viable cells, comprising
   viable cells dispersed in a three-dimensional particulate, essentially non-cross-linked, chitosan core matrix encapsulated in a thermoplastic semipermeable membrane,
   wherein the chitosan core matrix containing dispersed cells is formed by precipitation of a chitosan solution containing said cells after the solution has been encapsulated in the thermoplastic semipermeable membrane.

2. The encapsulated viable cells of claim 1, wherein the cells are selected from the group consisting of neurosecretory cell lines, β-derived cell lines, fibroblasts, myocytes, and glial cells.

3. The encapsulated viable cells of claim 2, wherein the neurosecretory cell lines are PC12 cells, the β-cell-derived cell lines are NIT or RIN cells, and the glial cells are astrocytes.

4. An implantable immunoisolatory vehicle for providing a biologically active product to a host, the immunoisolatory vehicle comprising:
   (a) a core, comprising PC12 cells dispersed in a particulate, substantially non cross-linked chitosan core matrix, said cells being capable of secreting a selected biologically active product; and
   (b) an external macrocapsular membrane surrounding said core formed of a thermoplastic material free of said cells projecting externally thereof, permitting passage of said biologicaly active product between the host and the core through said membrane, said core and said membrane being free of interlinking at the interface therebetween, and said core surrounded by said membrane being formed by precipitating a chitosan solution containing said cells after said solution has been surrounded by said membrane.

* * * * *